US011793488B2

(12) United States Patent
Poland

(10) Patent No.: US 11,793,488 B2
(45) Date of Patent: Oct. 24, 2023

(54) ERGONOMIC DISPLAY AND ACTIVATION IN HANDHELD MEDICAL ULTRASOUND IMAGING DEVICE

(71) Applicant: KONINKLIJKE PHILIPS N.V., Eindhoven (NL)

(72) Inventor: Mckee Dunn Poland, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 96 days.

(21) Appl. No.: 16/969,330

(22) PCT Filed: Feb. 14, 2019

(86) PCT No.: PCT/EP2019/053607
§ 371 (c)(1),
(2) Date: Aug. 12, 2020

(87) PCT Pub. No.: WO2019/158618
PCT Pub. Date: Aug. 22, 2019

(65) Prior Publication Data
US 2021/0045713 A1 Feb. 18, 2021

Related U.S. Application Data

(60) Provisional application No. 62/631,566, filed on Feb. 16, 2018.

(51) Int. Cl.
*A61B 8/00* (2006.01)
*G06F 1/3231* (2019.01)
(Continued)

(52) U.S. Cl.
CPC .......... *A61B 8/4455* (2013.01); *A61B 8/4427* (2013.01); *A61B 8/462* (2013.01);
(Continued)

(58) Field of Classification Search
CPC ... A61B 8/4427; A61B 8/4444; A61B 8/4455; A61B 8/46; A61B 8/462; A61B 8/467;
(Continued)

(56) References Cited

U.S. PATENT DOCUMENTS 8,055,305 B2 * 11/2011 Cho ...................... G06F 1/1684
455/550.1
9,295,444 B2 * 3/2016 Schwartz ............. A61B 8/4483
(Continued)

FOREIGN PATENT DOCUMENTS

EP 3293622 B1 * 10/2019 ........... G06F 1/1613
JP 2003299647 A 10/2003
(Continued)

OTHER PUBLICATIONS

International Search Report and Written Opinion for International Application No. PCT/EP2019/053607, filed Feb. 14, 2019, 15 pages.

*Primary Examiner* — Christopher Koharski
*Assistant Examiner* — Taylor Deutsch

(57) ABSTRACT

In an embodiment, a medical device is disclosed. The medical (imaging) device comprises a housing configured for handheld use, a transducer array, a display coupled to the housing, a plurality of sensors distributed about a periphery of the housing and configured to detect when a hand of an operator is positioned around the housing, and a computing device disposed within the housing, wherein the computing device is in communication with the transducer array, the display, and the sensors. The computing device is operable to: monitor the sensors, determine whether a reading from a first sensor at a first edge of the periphery of the housing exceeds a threshold, set the first edge as a primary edge
(Continued)

based at least in part on the reading from the first sensor, and orient the display such that the primary edge is at the bottom of the display.

16 Claims, 5 Drawing Sheets

(51) Int. Cl.
  *G01S 7/52* (2006.01)
  *G06F 1/16* (2006.01)
(52) U.S. Cl.
  CPC ............ *A61B 8/56* (2013.01); *G01S 7/52096* (2013.01); *G06F 1/3231* (2013.01); *G01S 7/5208* (2013.01); *G06F 1/1626* (2013.01); *G06F 2200/1637* (2013.01)
(58) Field of Classification Search
  CPC ... A61B 8/54; G01S 7/52079; G01S 7/52082; G06F 1/1626; G06F 2200/1614; G06F 2200/1637
  See application file for complete search history.

(56) References Cited

U.S. PATENT DOCUMENTS

| | | | |
|---|---|---|---|
| 9,350,912 B2* | 5/2016 | Suki | ................ H04N 21/41407 |
| 9,541,993 B2* | 1/2017 | Balasundaram | ........ G06F 3/011 |
| 9,814,445 B2 | 11/2017 | Cheng et al. | |
| 10,145,946 B2 | 12/2018 | Kashima et al. | |
| 10,175,654 B2* | 1/2019 | Berardinelli | ........... G04G 21/08 |
| 10,517,569 B2* | 12/2019 | Weitzel | ................ A61B 8/461 |
| 2006/0232164 A1 | 10/2006 | Kondo et al. | |
| 2007/0239029 A1 | 10/2007 | Okabe et al. | |
| 2008/0048993 A1 | 2/2008 | Yano | |
| 2009/0198132 A1* | 8/2009 | Pelissier | ............. G01S 7/52084 600/443 |
| 2010/0016726 A1 | 1/2010 | Meier | |
| 2010/0145195 A1 | 6/2010 | Hyun | |
| 2012/0136256 A1 | 5/2012 | Nozaki et al. | |
| 2014/0307522 A1 | 10/2014 | Kashima et al. | |
| 2015/0011884 A1* | 1/2015 | Walker | ................. A61B 8/4455 600/447 |
| 2015/0038844 A1 | 2/2015 | Blalock et al. | |
| 2015/0103018 A1* | 4/2015 | Kamin-Lyndgaard | ....................... G06F 3/0443 345/173 |
| 2016/0074060 A1 | 3/2016 | Messerly et al. | |
| 2016/0253016 A1* | 9/2016 | Kim | ................. G06F 3/041661 345/173 |
| 2017/0220176 A1* | 8/2017 | Park | ...................... G06F 1/1694 |
| 2017/0336970 A1* | 11/2017 | Kim | .................... G06F 3/04883 |
| 2017/0357440 A1* | 12/2017 | Tse | ........................ G06F 3/0482 |

FOREIGN PATENT DOCUMENTS

| | | | | |
|---|---|---|---|---|
| JP | 2008027183 A | | 2/2008 | |
| JP | 2010131396 A | | 6/2010 | |
| JP | 2011067544 A | | 4/2011 | |
| JP | 2013165923 A | | 8/2013 | |
| JP | 2017153584 A | | 9/2017 | |
| KR | 1020160139518 A | | 12/2016 | |
| KR | 1020170055734 A | | 5/2017 | |
| WO | 03075769 A1 | | 9/2003 | |
| WO | WO-2017097348 A1 * | | 6/2017 | ........... G06F 1/1616 |
| WO | 2017222964 A1 | | 12/2017 | |
| WO | 2013104518 A1 | | 7/2018 | |

\* cited by examiner

ERGONOMIC DISPLAY AND ACTIVATION IN HANDHELD MEDICAL ULTRASOUND IMAGING DEVICE

RELATED APPLICATIONS

This application is the U.S. National Phase application under 35 U.S.C. § 371 of International Application No. PCT/EP2019/053607, filed on Feb. 14, 2019, which claims the benefit of and priority to Provisional Application Ser. No. 62/631,566, filed Feb. 16, 2018. These applications are incorporated by reference herein.

TECHNICAL FIELD

The present disclosure relates generally to handheld medical scanning devices and, in particular, to a handheld medical scanning device configured to orient medical information on a display based at least in part on a grip a user has on the handheld medical scanning device.

BACKGROUND

As medical technology has advanced over the years, several different imaging modalities, e.g., magnetic resonance imaging (MRI), computed tomography (CT), x-ray, fluoroscopy, angiography, ultrasound, etc., have been developed to allow physicians to view anatomical structures within a patient's body without having to open the patient surgically. In the case of ultrasound, ultrasonic waves are emitted from ultrasonic transducers into the patient's body. The ultrasonic waves are partially reflected by discontinuities arising from tissue structures, red blood cells, and other features within the patient. Echoes from the reflected waves are received by the ultrasonic transducers and processed to produce an ultrasonic image. The ultrasonic image is generally outputted to a display for viewing by a physician. Review of the displayed images often plays an integral role in a physician's diagnosis and treatment plan.

SUMMARY

Embodiments of the present disclosure provide improved systems and methods for orienting medical information on a display of a handheld medical scanning device and controlling its activation. In that regard, the present disclosure provides for a handheld medical scanning device featuring a plurality of sensors configured to detect a user's hand gripping the handheld medical scanning device. The handheld medical scanning device may be configured to switch from a low-energy sleep mode to an active mode in response to sensor readings indicating that a user's hand is in contact with the handheld medical scanning device. Remaining in the low-energy mode until a user's hand is detected advantageously extends battery life by reducing energy expenditure during times when the handheld medical scanning device is not in use. Additionally, the handheld medical scanning device may determine the position of the user's hand based on readings from the sensors and may orient medical information on a display based on the determined position of the user's hand. For example, the handheld medical scanning device may determine the position of the user's thumb and may orient medical information on the display such that the bottom of the information window is on the same side as the user's thumb when the handheld medical scanning device is held by the user. In many cases, a user's preferred viewing orientation will be when the bottom of the information window of the display is on the same side as the user's thumb. Accordingly, automatically orienting information window on the display in this way conveniently allows the user to pick up the handheld medical scanning device without regard the orientation of the handheld medical scanning device itself and trust that the display will nevertheless be in the user's preferred viewing orientation.

In one embodiment, an ultrasound imaging device is disclosed. The ultrasound imaging device comprises a housing configured for handheld use, an ultrasound transducer array coupled to the housing and configured obtain ultrasound (imaging) data while positioned adjacent to a body of a patient, a display coupled to the housing, a plurality of sensors distributed about a periphery of the housing and configured to detect when a hand of an operator is positioned around the housing, and a computing device disposed within the housing. The computing device is in communication with the ultrasound transducer array, the display, and the plurality of sensors. The computing device is operable to monitor the plurality of sensors, determine whether a reading from a first sensor of the plurality of sensors at a first edge of the periphery of the housing exceeds a threshold, set the first edge as a primary edge based at least in part on the reading from the first sensor, and orient medical information on the display such that the primary edge is at the bottom of the information window of the display.

In some embodiments, the computing device is further operable to: switch the ultrasound imaging device from a sleep mode to an active mode in response to determining that the reading from the first sensor exceeds the threshold. In some embodiments, the ultrasound imaging device expends only enough power to monitor the plurality of sensors while in the sleep mode. In some embodiments, the computing device is further operable to: power on the display in response to switching the ultrasound imaging device from the sleep mode to the active mode. In some embodiments, the computing device is further operable to: determine that the first edge is gripped by a thumb of the operator based on at least in part on the reading from the first sensor. In some embodiments, the computing device is further operable to: determine that a reading from a second sensor at a second edge indicates that the second edge is gripped by a finger of the operator other than the thumb. In some embodiments, the computing device is further operable to: determine that a reading from a third sensor at a third edge indicates that the third edge is gripped by an interdigital webbing of the operator's hand. In some embodiments, the plurality of sensors are capacitance sensors. In some embodiments, the ultrasound device further comprises an accelerometer, wherein the computing device is operable to set the first edge as the primary edge based at least in part on a reading from the accelerometer. In some embodiments, the computing device is operable to: activate the ultrasound transducer array to obtain ultrasound (imaging) data.

In one embodiment, a method of operating a handheld ultrasound imaging device is disclosed. The method comprises monitoring, by a computing device of the handheld ultrasound imaging device, a plurality of sensors distributed about a periphery of a housing of the handheld ultrasound imaging device; determining, by the computing device, whether a reading from a first sensor at a first edge of the housing exceeds a threshold; setting, by the computing device, the first edge as a primary edge based at least in part on the reading from the first sensor; and orienting, by the computing device, an information window, including ultrasound based hemodynamic parameters and/or ultrasound images, of the display of the handheld ultrasound device such that the primary edge is at the bottom of the display.

In some embodiments, the method further comprises switching, by the computing device, the handheld ultrasound imaging device from a sleep mode to an active mode in response to determining that the reading from the first sensor exceeds the threshold. In some embodiments, setting the first edge as the primary edge comprises determining, by the computing device, that the first edge is gripped by a thumb of an operator. In some embodiments, determining that the first edge is gripped by the thumb of the operator comprises determining that the reading from the first sensor exceeds the reading from a second sensor. In some embodiments, determining that the first edge is gripped by the thumb of the operator comprises referencing a stored handedness preference.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1A:
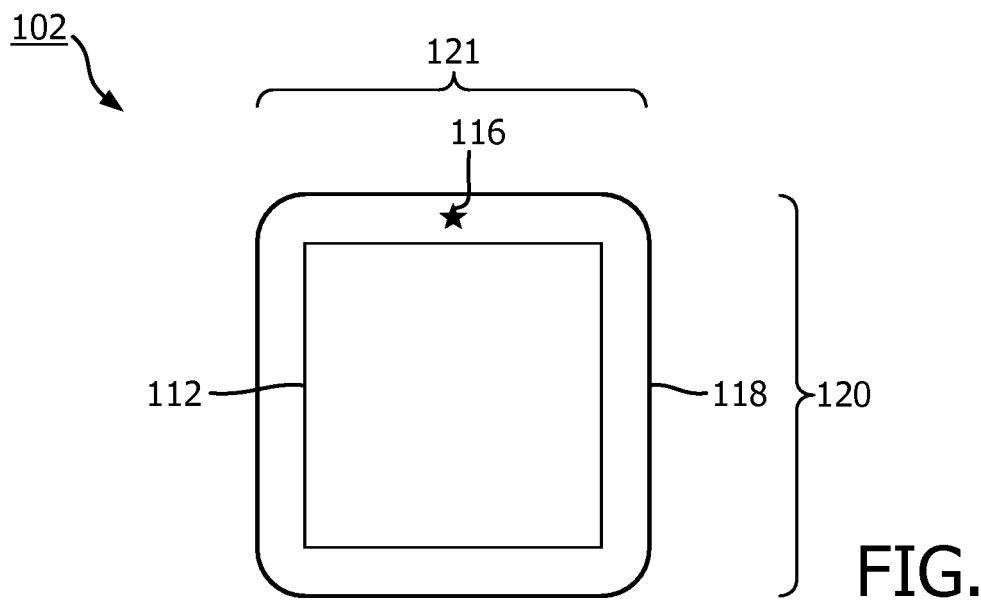
FIG. 1A is a diagrammatic top view of a handheld medical scanning device, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Aspects of the present disclosure relate to a handheld medical scanning device having an electronically rotatable display on the top surface of the handheld medical scanning device and an active medical scanner component on the bottom surface of the handheld medical scanning device. The medical scanner component may be in contact with a patient when in use. The handheld medical scanning device may take the form of a rounded square (as depicted in, e.g., FIG. 1A). The lateral faces, also referred to herein as edges, of the handheld medical scanning device may be thick enough, and the other dimensions small enough, that the most natural way to hold the device is by its lateral faces. When the handheld medical scanning device is held in this way, the display may be viewable by a user while the medical scanner component at the bottom surface is pressed against a patient's body. Thus, a user's hand may partially enclose the handheld medical scanning device such that the user's thumb, interdigital webbing, and forefinger touch three of the four sides of the handheld medical scanning device to form a comfortable grip. In such a grip, the interdigital webbing of the user's hand may be said to be on an included edge, that is, an edge between an edge gripped by the user's thumb and an edge gripped by the user's forefinger opposite the edge gripped by the user's thumb.

One aspect of the present disclosure relates to automatically orienting the information window of the display so that displayed text/images are comprehensible to the user holding the handheld medical scanning device while using it, e.g., while performing ultrasound scanning. In that regard, the handheld medical scanning device may determine which edge should be at the bottom of the rotatable display. The edge that the handheld medical scanning device determines should be at the bottom of the rotatable display (information window) is referred to herein as a primary edge. The handheld medical scanning device may orient the rotatable display so that the primary edge is at the bottom of the rotatable display. Several techniques for identifying the primary edge, e.g., based on a user's grip and/or on an accelerometer reading, are described herein.

For example, in a typical grip, the user's thumb is on the edge that should be at the bottom of the rotatable display. This is true whether the user is holding the handheld medical scanning device in their left or right hand, and is also true whether the user is scanning himself/herself or another person. That the edge gripped by the user's thumb should be at the bottom of the rotatable display is also true whether the device is in contact with the patient, as while imaging with the handheld medical scanning device, or held up in the air for easy viewing of results after imaging. Therefore, the handheld medical scanning device may identify the primary edge by determining which edge is gripped by the user's thumb. The handheld medical scanning device may beneficially orient the rotatable display so that the edge gripped by the user's thumb, e.g., the primary edge, is at the bottom of the display. These and other aspects will be discussed in greater detail herein below.

Figure 1B:
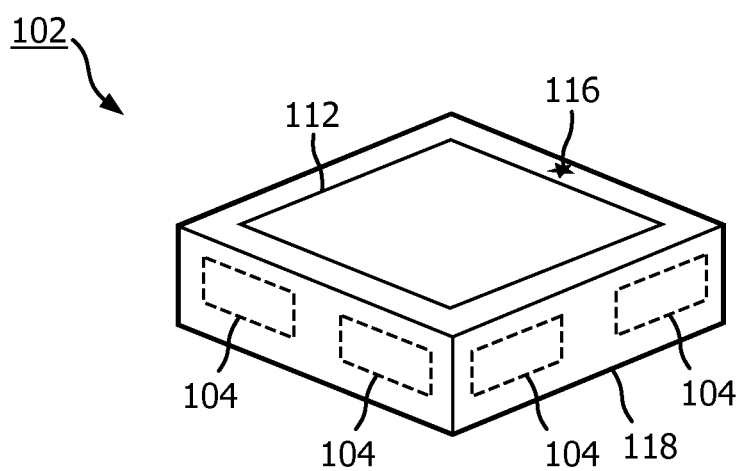
FIG. 1B is a diagrammatic perspective view of a handheld medical scanning device, according to aspects of the present disclosure.
Figure 1C:
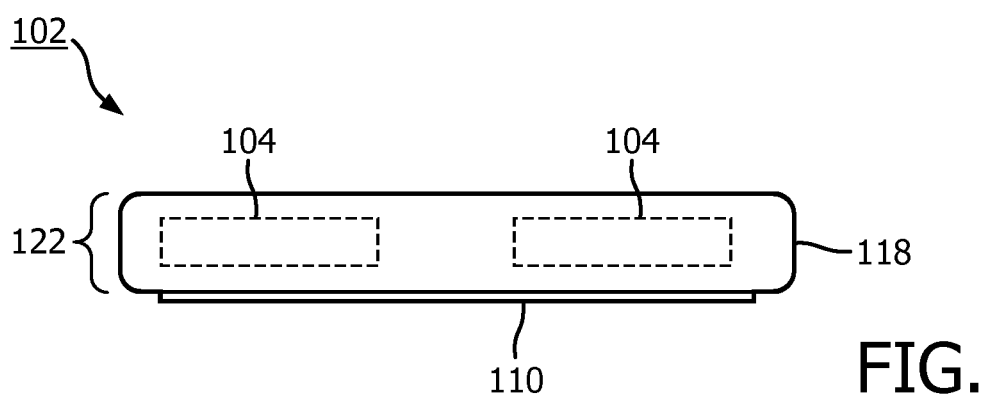
FIG. 1C is a diagrammatic side view of a handheld medical scanning device, according to aspects of the present disclosure.

Turning now to FIGS. 1A-1C, shown therein are various diagrammatic views of a handheld medical scanning device 102, according to aspects of the present disclosure. As illustrated, the handheld medical scanning device 102 may include a plurality of sensors 104, a scanning (imaging) element 110, a display 112, a reference mark 116, and a housing 118 having a length 120, width 121, and depth 122. The plurality of sensors 104 may be disposed within and distributed about a periphery of the housing 118. The display 112 and the imaging element 110 may be disposed on top and bottom faces of the handheld medical scanning device 102, respectively. Additional aspects of the handheld medical scanning device 102 and the various features thereof will be described in greater detail below.

The handheld medical scanning device 102 may be operable to obtain medical data or images of a patient's anatomy via the scanning (imaging) element 110. For example, the scanning (imaging) element 110 may be placed in contact with or in proximity to a patient's skin overlying an area to be investigated or imaged. The scanning element 110 may then emit one or more types of energy and receive back energy reflected by the patient's bodily structures. This reflected energy may be used to form representative data (such as images) of the patient's anatomy. In that regard, the scanning element 110 may comprise an infrared scanner, an ultrasound scanner, an optical imaging element, an Optical Coherence Tomography (OCT) scanner, a Computed Tomography (CT) scanner, an X-Ray scanner, or combinations thereof. Accordingly, the handheld medical scanning device 102 may obtain any combination of thermal data, ultrasound data, optical data, OCT images, CT images, and X-ray images. In particular, when the scanning element 110 comprises an ultrasound scanner, the scanner element 110 may comprise one or more ultrasound transducers configured to emit ultrasonic waves into the bodily tissues of the patient. The ultrasonic waves may be partially reflected by discontinuities arising from tissue structures, red blood cells, and other features within the patient. Echoes from the reflected ultrasonic waves may be received by the ultrasonic transducers and processed by the handheld medical scanning device 102, in particular processor 206, to derive a hemodynamic parameter and/or produce an ultrasonic image, based on the acquired ultrasound data. In that regard, the handheld medical scanning device 102 can be referenced as an ultrasound (imaging) device.

The ultrasound element 110 can include one or more ultrasound transducers. For example, a plurality of ultrasound transducers can be arranged in an array. For example, an ultrasound transducer array can include any suitable number of individual transducers between 2 transducers and 1000 transducers, including values such as 2 transducers, 4 transducers, 36 transducers, 64 transducers, 128 transducers, 500 transducers, 812 transducers, and/or other values both larger and smaller. The ultrasound element 110 can be any suitable configuration, such as phased array including a planar array, a curved array, etc. For example, the ultrasound element 110 can be a one-dimensional array, 1.x-dimensional array, such as a 1.5-dimensional array, or a two-dimensional array, in some instances. In that regard, the ultrasound transducer or transducer array 110 can be configured obtain one-dimensional, two-dimensional, and/or three-dimensional images of the anatomy of the patient. The ultrasound element 110 can be a matrix array, including one or more segments of ultrasound elements (e.g., one or more rows, one or more columns, and/or one or more orientations) that can be uniformly or independently controlled and activated. The ultrasound element 110 can include any suitable transducer type, including a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof.

The acquired medical data and derived therefrom hemodynamic parameters or images, e.g., ultrasound images, of the patient's anatomy may be outputted to the display 112 for review. In some cases, the handheld medical scanning device 102 may analyze the obtained data (images) and may output its findings to the display 112. For example, the handheld medical scanning device 102 may highlight areas of interest within the images, may display measurements of anatomical structures within the images, may display hemodynamic value (such as ejection fraction or cardiac output) or/and its variation with time (waveform), may make recommendations based on the values or images, or combinations thereof. The outputted findings may be superimposed over the images to which they relate or may be displayed separately.

The handheld medical scanning device 102 may be further operable to display other medical data in the information window of its display such as a treatment plan, a medication schedule, test results, an appointment schedule, a progress report, archived images, a patient history, or combinations thereof. Such medical data may be stored on the handheld medical scanning device 102 itself or may be stored remotely, e.g., in a hospital record system. In that regard, the handheld medical scanning device 102 may comprise a radiofrequency transceiver to facilitate wireless communication with the hospital record system in order to allow a user to access remotely stored medical data using the handheld medical scanning device 102.

A user of the handheld medical scanning device 102 may input instructions to control the operation of the handheld medical scanning device 102 via one or more buttons and/or via the display 112. In that regard, the display 112 may comprise a capacitive or resistive touch screen and may serve as a graphical user interface (GUI). A user may issue touch-based instructions on the display 112 to switch between various screens and a home screen, in order to zoom in on one or more regions of a waveform, an image, e.g., an ultrasound image, in order to enter one or more preferences, e.g., a handedness preference, in order to input information such as a patient's age, weight, sex, etc., in order to access medical data, in order to activate or deactivate scanning with the scanning element 110, or combinations thereof.

The handheld medical scanning device 102 may be sized and shaped for handheld use. Though variously illustrated as having the perimeter of a square or rounded square, the handheld medical scanning device 102 may in some cases have a circular perimeter, a triangular perimeter, a rectangular perimeter, a pentagonal perimeter, a hexagonal perimeter, or some other perimeter. The housing 118 may have a length 120, width 121, and depth 122 suitable to enable a user to securely grip, with either hand or with both hands, the handheld medical scanning device 102 while imaging operations and/or other operations are performed. By way of particular example, but without limitation, the housing 118 may have a length 120 of seven centimeters, a width 121 of seven centimeters, and a thickness of two centimeters. Such dimensions would advantageously allow the handheld medical scanning device 102 to be used with a single hand grip by virtually all users. A user may maintain a single hand grip on the handheld medical scanning device 102 by gripping the handheld medical scanning device 102 with their thumb on one lateral face of the housing 118 and their index finger on an opposing lateral face of the housing 118. Lateral faces of the housing 118 may be referred to herein as edges.

Sensors 104 within the housing 118 may be configured to detect when the handheld medical scanning device 102 is gripped by the hand of a user. In that regard, the sensors 104 may be positioned within and distributed about a periphery of the housing 118. The sensors 104 may be located on lateral faces of the housing 118, within housing material making up the lateral faces of housing 118, just behind housing material making up the lateral faces of housing 118, or combinations thereof. Accordingly, sensors 104 may come in direct contact with the skin of a user's hand or may be separated from direct contact with the user's skin by a layer of housing material. In some cases, lateral faces of housing 118 may comprise one or more regions of reduced housing material thickness relative to other regions of the housing 118. Sensors 104 may be located within these regions of reduced housing material thickness in order to reduce effects of the housing material on the ability of sensors 104 to detect the presence of a user's hand around the housing 118. Sensors 104 may be connected by a single flexible circuit disposed within and wrapped about the periphery of the housing 118, or sensors 104 may be independent units. Though FIGS. 1B and 1C illustrate two sensors 104 at each lateral face of the housing 118, the handheld medical scanning device 102 may comprise one sensor 104 at each lateral face, three sensors 104 at each lateral face, four sensors 104 at each lateral face, five sensors 104 at each lateral face, some other number of sensors 104 at each lateral face, or combinations thereof. In some cases, the number of sensors 104 may be chosen to provide detection capabilities along the entirety of a lateral face. Sensors 104 may comprise thermal sensors, capacitive sensors, impedance sensors, fingerprint readers, or combinations thereof.

The handheld medical scanning device 102 may be configured to remain in a sleep mode until a user's grip is detected. The sleep mode may be a low-energy mode configured to advantageously conserve battery life by reducing energy expenditure during times when the handheld medical scanning device 102 is not in use. While in the sleep mode, the handheld medical scanning device 102 may expend only enough power to monitor sensors 104. Accordingly, in some cases, battery life may be extended out to one, two, three or more months while the handheld medical scanning device 102 is in the sleep mode. The handheld medical scanning device 102 may be configured to enter the sleep mode if a threshold amount of time has elapsed without sensors 104 detecting a user's hand. For example, the handheld medical scanning device 102 may enter the sleep mode after contact has been absent for one second, two seconds, five seconds, ten seconds, thirty seconds, one minute, two minutes, five minutes, ten minutes, or for some other amount of time.

How fast the handheld medical scanning device 102 enters the sleep mode may be variable based on one or more device metrics, e.g., battery life. For example, the handheld medical scanning device 102 may enter the sleep mode faster when battery life is lower. In some cases, how fast the handheld medical scanning device 102 enters sleep mode may change in real time with battery life such that any change in battery life results in a change in how quickly the handheld medical scanning device 102 enters sleep mode. In other cases, one or more thresholds may be established wherein crossing a threshold of battery life results in a change how fast the handheld medical scanning device 102 enters the sleep mode.

The handheld medical scanning device 102 may be configured to switch from the sleep mode to an active mode in response to the sensors 104 detecting that a user has gripped the handheld medical scanning device 102. The active mode may be a mode in which additional device capabilities are active. For example, in the active mode, a user may be able to enter or modify preferences, e.g., handedness preferences or how quickly to enter sleep mode or active mode, may be able to review medical data stored locally and/or remotely, etc. In some cases, the active mode may be a mode in which the full range of device capabilities are active. The handheld medical scanning device 102 may be configured to switch from the sleep mode to an active mode only after the user has gripped the handheld medical scanning device 102 for a certain amount of time, e.g., longer than momentarily, half a second, one second, two seconds, three seconds, four seconds, five seconds, or some other amount of time. As similarly described above, how quickly the handheld medical scanning device 102 switches from the sleep mode to the active mode may be variable based on one or more device metrics, e.g., battery life. For example, the handheld medical scanning device 102 may enter the active mode slower when battery life is lower. In some cases, how fast the handheld medical scanning device 102 enters active mode may change in real time with battery life such that any change in battery life results in a change in how quickly the handheld medical scanning device 102 enters active mode. In other cases, one or more thresholds may be established wherein crossing a threshold of battery life results in a change how fast the handheld medical scanning device 102 enters the active mode.

The handheld medical scanning device 102 may switch into active mode from the sleep mode when any grip is detected regardless of whether a specific grip, e.g., a user's thumb and index finger gripping opposing lateral faces, can be determined. In that regard, the handheld medical scanning device 102 may switch into the active mode from the sleep mode when sensors 104 at any lateral face or any combination of lateral faces produce readings indicating contact of a user's hand with the lateral face or faces. A user may initially pick up the handheld medical scanning device 102 in such a way that a specific grip cannot be identified. For example, in some cases, a specific grip might not be identified when the user picks up the handheld medical scanning device 102 quickly with a haphazard grip or an inconsistent grip that may be changed or adjusted one or more times before the user decides on a comfortable working grip. In such cases, it would be advantageous to switch the handheld medical scanning device 102 from the sleep mode to the active mode even before a specific grip can be determined so that the user has access to device capabilities of the active mode as soon as the user settles on a grip.

In other cases, e.g., when the handheld medical scanning device 102 is particularly low on battery, the handheld medical scanning device 102 may only switch to the active mode from the sleep mode when the handheld medical scanning device 102 detects a specific grip or detects contact of the user's hand with opposing lateral faces, even if the specific grip, e.g., which digit is in contact with which face, cannot be identified. Switching to the active mode in this way would allow the handheld medical scanning device 102 to remain in the sleep mode longer and therefore advantageously conserve battery life and limit the risk of the handheld medical scanning device 102 running out of battery during use.

The handheld medical scanning device 102 may, even in the sleep mode in some cases, track one or more device metrics such as battery life and may modify its behavior based on current metrics. For example, as suggested above, the handheld medical scanning device 102 may switch into the active mode from the sleep mode when any grip is detected regardless of whether a specific grip can be determined when the handheld medical scanning device 102 is not low on battery and may switch into the active mode from the sleep mode only when a specific grip or user contact with opposing lateral faces is detected when the handheld medical scanning device 102 is low on battery. Battery life may be low when it falls below 50%, below 40%, below 30%, below 25%, below 20%, below 15%, below 10%, below 5%, within 5% of an average amount expended for an imaging procedure, within 5% of an average amount expended during a single use, or combinations thereof.

Whether or not a user's hand is in contact with the handheld medical scanning device 102 may be determined by comparing readings from the sensors 104 to a threshold reading, to a stored profile, or to combinations thereof. For example, the handheld medical scanning device 102 may determine that a user's hand is in contact with the handheld medical scanning device 102 and enter the active mode from the sleep mode in response to determining that a capacitance reading exceeds a threshold, determining that an impedance reading exceeds a threshold, determining that a thermal reading exceeds a threshold, determining that a detected fingerprint matches a fingerprint stored in a user profile, or combinations thereof.

Once the user has a grip on the handheld medical scanning device 102, the user may wish to perform an imaging operation, review medical data, etc. These activities may involve the user observing and interacting with the display 112, which displays an information window including ultrasound derived hemodynamic parameters and/or ultrasound images. In many cases, a user's preferred viewing orientation will be when the bottom of information window of the display 112 is on the same side as the user's thumb. As the term is used herein, the bottom of the display 112 refers not to the bottom of the physical hardware making up the display 112 but rather to the side of the display 112 corresponding to the bottom of whatever content is displayed on the display 112 as determined by a conventional viewing orientation of the content. For example, in the case of English text displayed on the display 112, the conventional viewing orientation is one in which an English speaking user may read and comprehend the text by proceeding word-by-word from the user's left to the user's right while viewing the text on the display 112. In this example, the bottom of the content is, in the case of multi-lined text, the last line of the text while the top of the content is the first line of the text when the text is displayed in the conventional viewing orientation. In this example, the side of the display 112 that is closest to the last line of text while being parallel to the last line of text is the side of the display that corresponds to the bottom of the text and is therefore the bottom of the display 112.

The handheld medical scanning device 102 may be configured to determine a position of the user's hand around the handheld medical scanning device 102, e.g., determine a specific grip the user has on the handheld medical scanning device 102, and orient the display 112 based on the determined hand position. As the term is used herein, orienting the display 112 does not refer to orienting the physical hardware making up the display 112 but rather to orienting the content displayed on the display 112. Specifically, but without limitation, the handheld medical scanning device 102 may be configured to automatically determine the position of the user's thumb and automatically orient the display 112 such that the bottom of the display 112 is on the same side as the user's thumb. Given that the user's preferred viewing orientation is typically one in which the bottom of the display 112 is on the same side as the user's thumb, automatically orienting the display 112 in this way conveniently allows the user to pick up the handheld medical scanning device 102 without regard the orientation of the handheld medical scanning device 102 itself and trust that the display 112 will nevertheless be in the user's preferred viewing orientation.

The handheld medical scanning device 102 may determine the position of the user's hand based at least in part on readings from sensors 104. In some cases, the position of the user's hand may be determined based at least in part on comparing readings from the sensors 104 to one or more threshold readings established for digits of a user's hand. For example, readings from the sensors 104 may be compared to a threshold reading established for a user's thumb, a threshold reading established for a user's index finger, a threshold reading established for a user's interdigital webbing between the user's thumb and index finger, or to combinations thereof. Such thresholds may be established as thresholds for individual sensor readings and/or as thresholds for readings by a group of sensors 104, e.g., a group of sensors 104 consisting of sensors 104 located at a given lateral face of the housing 118. In that regard, the handheld medical scanning device 102 may determine that a user's thumb is in contact with a lateral face of the housing 118 when either the group reading or one or more individual readings of sensors 104 on the lateral face exceeds the threshold reading for a user's thumb. The positions of the user's index finger and interdigital webbing may be determined in the same way. The threshold readings may be thermal readings, capacitance readings, impedance readings, finger prints, or combinations thereof. The threshold readings may be stored on the handheld medical scanning device 102 itself, e.g., in a memory of the handheld medical scanning device 102, or remotely.

The handheld medical scanning device 102 may determine the position of a user's hand by comparing readings of two or more sensors 104 to each other. For example, when readings from the sensors 104 indicate that the user's hand is in contact with opposing lateral faces of the housing 118, the handheld medical scanning device 102 may determine that the lateral face whose sensors 104 exhibit the strongest readings is gripped by the user's thumb while the opposing lateral face is gripped by the user's index finger. The lateral face determined to be gripped by the user's thumb may be the lateral face with the strongest single sensor reading or the lateral face with the strongest sensor group reading.

In some cases, the handheld medical scanning device 102 may consider the length, width, area, or combinations thereof, of a positive reading group of sensors 104 on a lateral face of the housing 118 to determine the position of the user's hand on the handheld medical scanning device 102. A positive reading group may be a group of sensors 104 whose readings are positive for user contact. The position of the user's hand may be determined by comparing the length, width, and area of the positive reading group of sensors 104 to length, width, and area thresholds established for positive reading groups indicating contact with a user's thumb, index finger, or interdigital webbing. When a positive reading group exceeds an established threshold, the handheld medical scanning device 102 may determine that the lateral face hosting the positive reading group is gripped by the portion of the user's hand corresponding to the exceeded threshold. The position of the user's hand may also be determined by comparing the length, width, and area of a positive reading group of sensors 104 located at one lateral face may with the length, width, and area of a positive reading group of sensors 104 located at another lateral face. For example, when positive reading groups are detected on opposing lateral faces of the housing 118, the positive reading group with the greatest area may be determined to be gripped by the user's thumb.

In some cases, when contact is detected on opposing lateral faces of the housing 118, the handheld medical scanning device 102 may assume that one lateral face is gripped by an index finger of a user and the opposing lateral face is gripped by the thumb of the user. In such circumstances the handheld medical scanning device 102 can simply determine, e.g., using the techniques described above, which lateral face is gripped by the user's thumb and orient the display 112 accordingly.

In other cases, however, contact may only be detected on adjacent lateral faces and not on opposing lateral faces. When contact is detected on adjacent lateral faces, the handheld medical scanning device 102 may assume that the adjacent lateral faces are gripped by a user's thumb on one lateral face and by the user's interdigital webbing on the other lateral face. In order to determine which lateral face is gripped by the user's thumb, the handheld medical scanning device 102 may consult a handedness preference stored on the handheld medical scanning device 102 or stored remotely. If the handedness preference indicates that the user prefers to grip the handheld medical scanning device 102 in their right hand, the handheld medical scanning device 102 may determine that the gripped lateral face which would be the furthest clockwise relative to the other gripped lateral face when the handheld medical scanning device 102 is viewed from above (as in FIG. 1A) is the lateral face gripped by the user's thumb. Similarly, if the handedness preference indicates that the user prefers to grip the handheld medical scanning device 102 in their left hand, the handheld medical scanning device 102 may determine that the gripped lateral face which would be the furthest counter-clockwise relative to the other gripped lateral face when the handheld medical scanning device 102 is viewed from above (As in FIG. 1A) is the lateral face gripped by the user's thumb.

In still other cases, the handheld medical scanning device 102 may not be able to determine the position of the user's thumb. When this occurs, the handheld medical scanning device 102 may orient the display 112 based on information from an accelerometer. The accelerometer may be a 3-axis accelerometer mounted at a known location in the handheld medical scanning device 102. For example, the accelerometer may be mounted such that the surface of the display 112 is parallel to the accelerometer's XY plane while the accelerometer +Z axis is perpendicular to the bottom face of the handheld medical scanning device 102. The handheld medical scanning device 102 may set the primary edge according to the signs of the X and Y components of the gravity vector, choosing one of the 4 sides from the mapping of +X/+Y, +X/−Y, −X/+Y, −X/−Y. If the gravity vector is less than a minimum specific threshold of degrees from the +Z axis, then then the primary edge may not be determinable based on accelerometer readings. In some embodiments, the device 102 can include a gyroscope in addition to or in lieu of the accelerometer.

The display 112 may have a default orientation, and the handheld medical scanning device 102 may orient the display 112 in the default orientation when the user's grip cannot be determined and/or readings from the accelerometer are insufficient to inform orientation of the display 112. For the user's convenience, a reference mark 116 may be located on the housing 118. A user may be able to determine, even if the handheld medical scanning device 102 is in the sleep mode, the default orientation of the display 112 based on the reference mark 116. For example, the user may know that the bottom of the display 112 is on the opposite side of the display 112 from the reference mark 116 when the display 112 is in the default orientation, or vice-versa. Accordingly, the user may grip the handheld medical scanning device 102 such that the default orientation is the user's preferred viewing orientation. Inclusion of the reference mark 116 may advantageously reduce user frustration in the event that one or more orienting processes fail. The reference mark 116 may be sized so as to be conspicuous for reference purposes. The reference mark 116 may comprise an image, a logo, a brand, a symbol, a functional element, a speaker, a number, a letter, alphanumeric text, a signature, or combinations thereof. In some cases, the reference mark 116 may be tactile to facilitate its location by visually impaired users.

Figure 2:
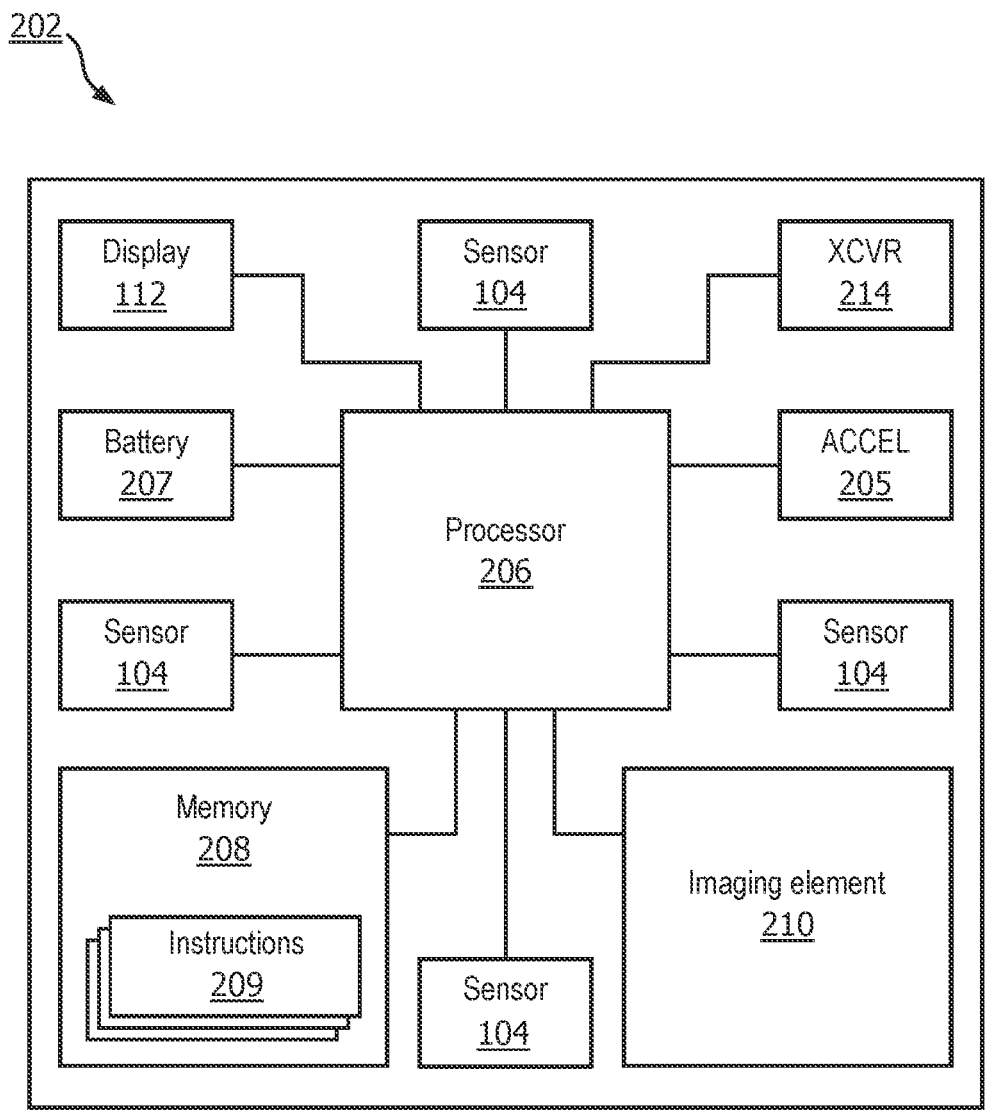
FIG. 2 is a diagrammatic schematic view of a handheld medical scanning device, according to aspects of the present disclosure.

Turning now to FIG. 2, shown therein is a diagrammatic schematic view of a handheld medical scanning device 202, according to aspects of the present disclosure. The handheld medical scanning device 202 may include a plurality of sensors 104, an accelerometer 205, a battery 207, a memory 208 with a plurality of instructions 209 stored therein, a scanning element 210, a display 112, and a radiofrequency transceiver 214 each in communication with a processor 206.

Sensors 104 may transmit readings to the processor 206 which may determine whether or not a user's hand is in contact with the handheld medical scanning device 202 based on the readings. The processor 206 may further determine the position of the user's hand around the handheld medical scanning device 202 based on the readings. For example, the processor 206 may compare readings from the sensors 104 to one or more thresholds stored in the memory 208 or may compare readings from different sensors 104 in order to determine the position of a user's hand. Based on the position of the user's hand, or based on readings from the accelerometer 205, the processor 206 may change the orientation of the display 112. The processor 206 may receive imaging data from the scanning (imaging) element 210 and output images (including associated with medical data) to the display 112. The processor 206 may also receive user input via the display 112. For example, the processor 206 may operate the radiofrequency transceiver 214 to obtain remotely stored medical data in response to a command inputted via the display 112 by a user. The memory 208 may store medical data, handedness preferences, threshold values, user profiles, fingerprint data, and a plurality of instructions 209 for execution by the processor, e.g., display orientation algorithms, among other things.

Figure 3A:
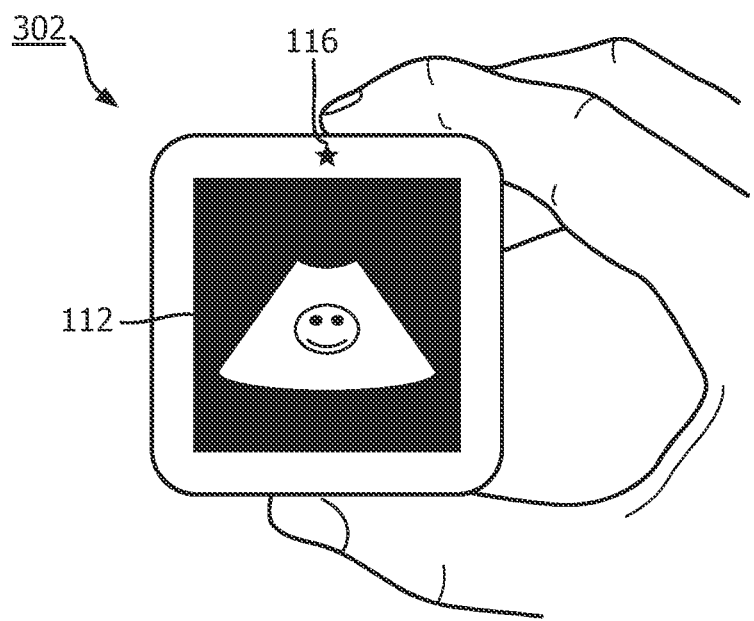
FIG. 3A is a diagrammatic top view of a handheld medical scanning device displaying ultrasound (imaging or monitoring) data in an information window while held in a first grip, according to aspects of the present disclosure.
Figure 3B:
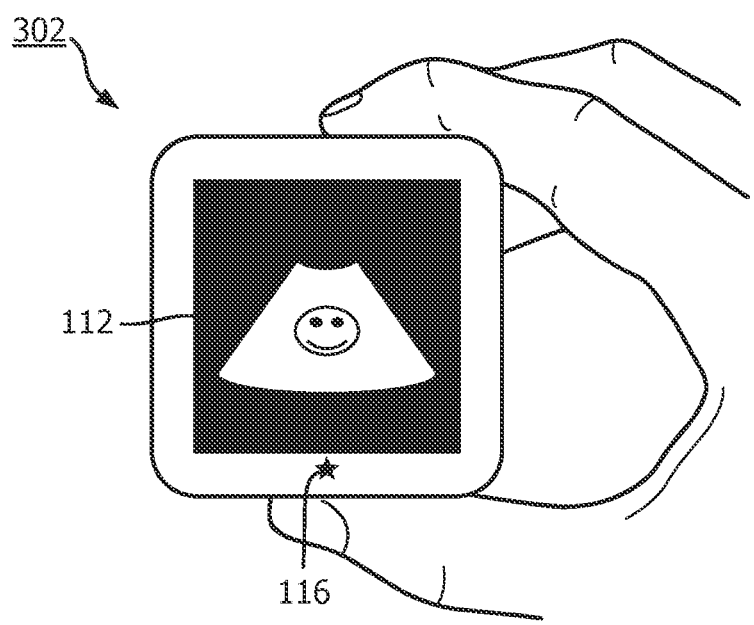
FIG. 3B is a diagrammatic top view of a handheld medical scanning device displaying ultrasound (imaging or monitoring) data while held in a second grip, according to aspects of the present disclosure.

FIGS. 3A and 3B are diagrammatic views of a handheld medical scanning device 302 comprising a reference mark 116 and a display 112 gripped by a user. In FIGS. 3A and 3B, the user is shown gripping the handheld medical scanning device 302 with their thumb on one lateral face and their index finger on a lateral face opposing that gripped by their thumb. Though the user is shown gripping the handheld medical scanning device 302 primarily with their thumb and index finger, the user may in some cases utilize a more secure grip by bringing their interdigital webbing into contact with the included edge located between the opposing edges gripped by the user's thumb and index finger. In each figure, the display 112 features an ultrasound image and is shown oriented such that the bottom of the display 112 is on the same side as the user's thumb; however, as is apparent from the change in position of the reference mark 116, the handheld medical scanning device 302 itself is rotated 180 degrees from FIG. 3A to FIG. 3B. This is intended to illustrate the ability of the handheld medical scanning device 302 to orient the display 112 based on the user's grip and irrespective of the orientation of the handheld medical scanning device 302 itself. As the user's grip changes, so too may the orientation of the display. So long as the user's grip is discernible, the display 112 will be automatically oriented in the user's preferred viewing orientation. Accordingly, the user may repeatedly pick up and set down the handheld medical scanning device 302 without the distraction of keeping track of the orientation of the handheld medical scanning device 302 itself.

Figure 4:
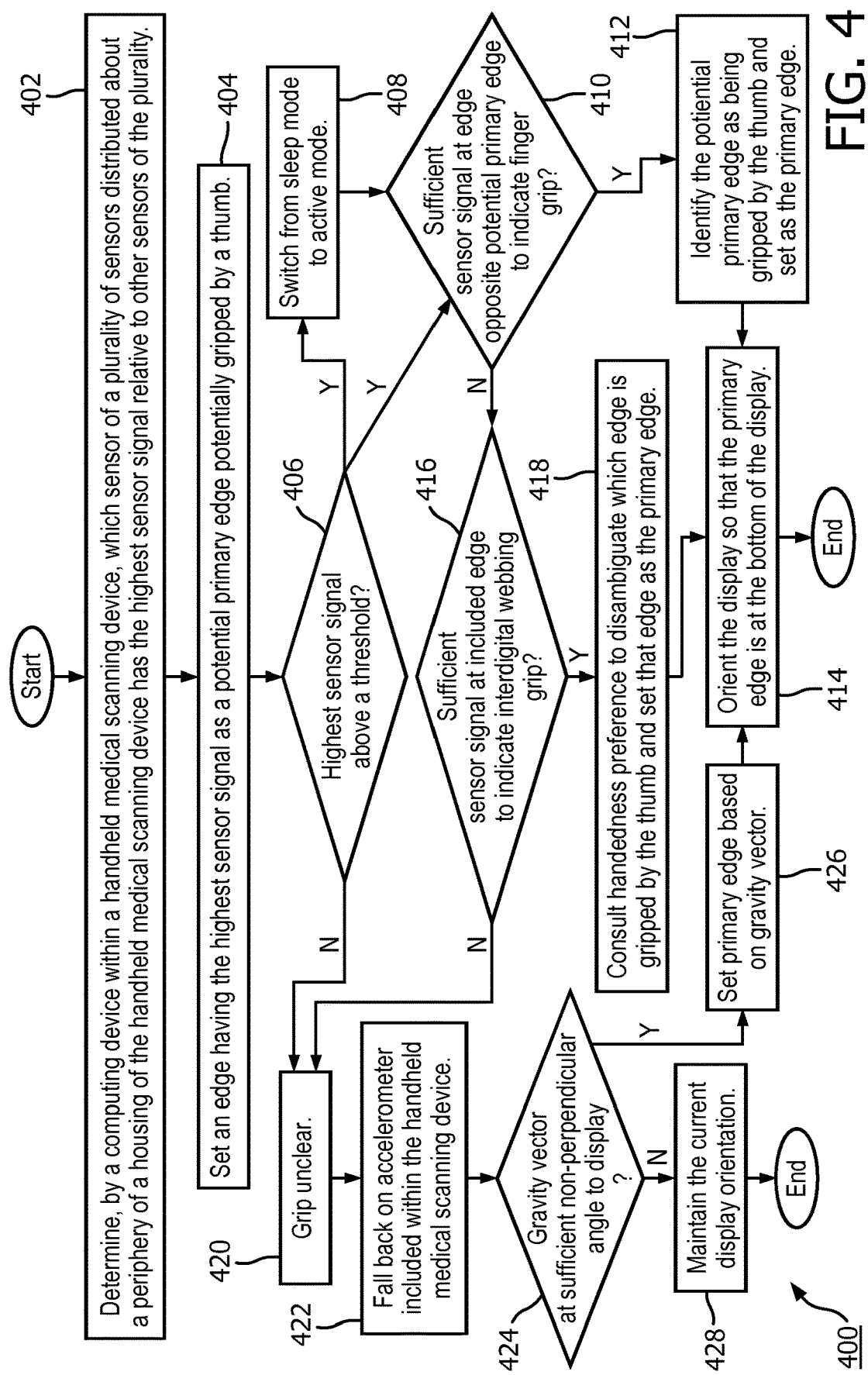
FIG. 4 is a flow chart of a method, according to aspects of the present disclosure.

Turning now to FIG. 4, a method 400 is described. The method 400 may be implemented by or with any of the handheld medical scanning devices described herein, e.g., handheld medical scanning devices 102, 202, and 302. The method begins at step 402 where a computing device within a handheld medical scanning device determines which sensor of a plurality of sensors distributed about a periphery of a housing of the handheld medical scanning device has the highest sensor signal relative to other sensors of the plurality. At step 404, an edge having the highest sensor signal is set as a potential primary edge potentially gripped by a user's thumb. At step 406, the computing device determines whether or not the highest sensor signal is above a threshold value.

If at step 406 the computing device determines that the highest sensor signal is not above a threshold value, then the method proceeds to step 420 where the computing device determines that the nature of the user's grip is unclear. Since the user's grip is unclear, at step 422 the computing device falls back on an accelerometer included within the handheld medical scanning device. At step 424, the computing device determines whether the gravity vector is at a sufficient non-perpendicular angle to a display of the handheld medical scanning device. If at step 424 the computing device determines that the gravity vector is not at a sufficient non-perpendicular angle to the display, then the method proceeds to step 428 where the computing device maintains the current orientation of the display. If, on the other hand, the computing device determines that the gravity vector is at a sufficient non-perpendicular angle to the display, then the method proceeds instead to step 426 where the computing device sets a primary edge based on the gravity vector. The method then proceeds to step 428 where the computing device orients the display so that the primary edge is at the bottom of the display.

If at step 406 the computing device determines that the highest sensor signal is above a threshold value, then the method proceeds to step 410 and optionally to step 408. At step 408, the computing device switches the handheld medical scanning device from a sleep mode to an active mode, and at step 410 the computing device determines whether there is sufficient sensor signal at the edge opposite the potential primary edge to indicate a finger grip, e.g., an index finger grip. If the computing device determines at step 410 that there is sufficient sensor signal to indicate a finger grip, then the method proceeds to step 412 where the computing device identifies the potential primary edge as being gripped by the user's thumb and therefore sets the potential primary edge as the primary edge. The method then proceeds to step 414 where the computing device orients the display so that the primary edge is at the bottom of the display.

If at step 410 the computing device determines that there is insufficient sensor signal at the edge opposite the potential primary edge to indicate a finger grip, then the method proceeds to step 416 where the computing device determines whether there is sufficient signal at an included edge between the potential primary edge and the edge opposite the primary edge to indicate a grip by an interdigital webbing. If the computing device determines that there is insufficient signal, then the method proceeds to step 420 and continues as before. If the computing device determines that there is sufficient signal, then the method continues to step 418 where the computing device consults a handedness preference to disambiguate which edge is gripped by the user's thumb and sets that edge as the primary edge. The method then proceeds to step 414 where the computing device orients the display so that the primary edge is at the bottom of the display.

Figure 5:
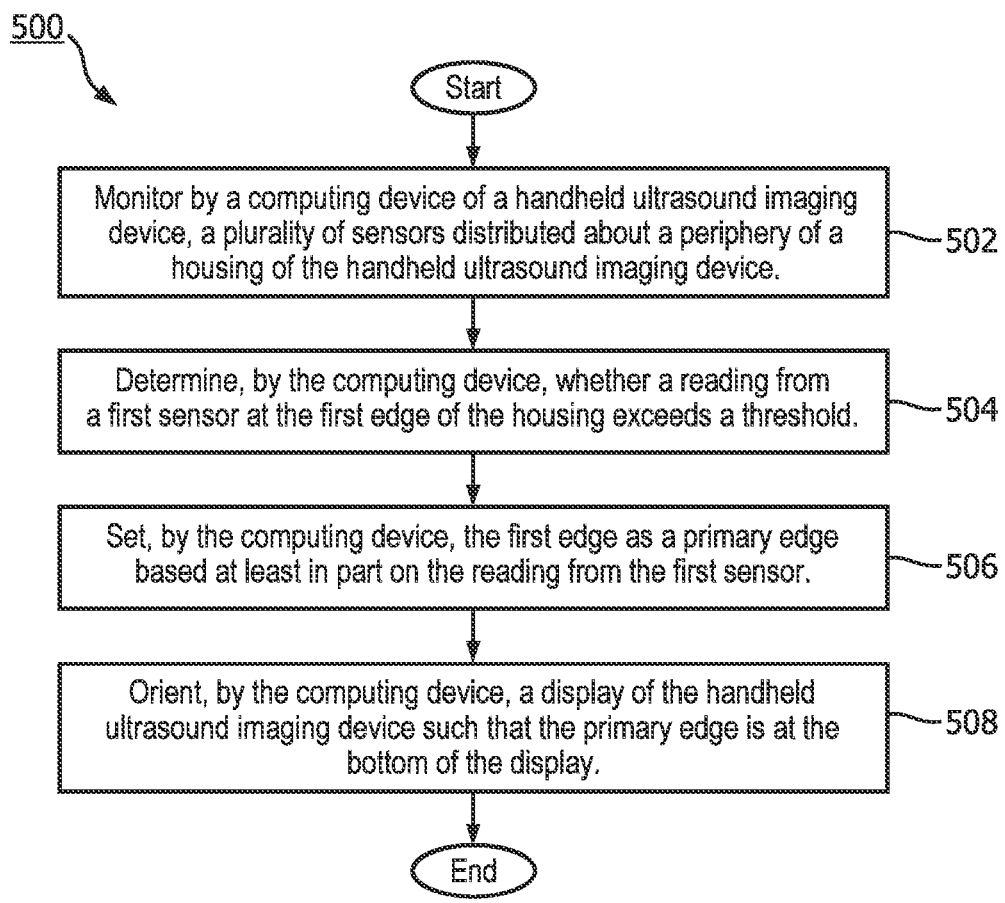
FIG. 5 is a flow chart of a method, according to aspects of the present disclosure.

Turning now to FIG. 5, a method 500 is described. The method 500 may be implemented by or with any of the handheld medical scanning devices described herein, e.g., handheld medical scanning devices 102, 202, and 302. The method begins at step 502 where a computing device of a handheld ultrasound imaging device monitors a plurality of sensors distributed about a periphery of a housing of the handheld ultrasound imaging device. The computing device then determines, at step 504, whether a reading from a first sensor at a first edge of the housing exceeds a threshold. At step 506, the computing device sets the first edge as a primary edge based at least in part on the reading from the first sensor. In some cases, setting the first edge as the primary edge comprises determining, by the computing device, that the first edge is gripped by a thumb of an operator. Determining that the first edge is gripped by the thumb of the operator may comprise determining that the reading from the first sensor exceeds the reading from a second sensor. In some cases, determining that the first edge is gripped by the thumb of the operator may comprise referencing a stored handedness preference. A display of the handheld ultrasound imaging device is oriented by the computing device at step 508 such that the primary edge is at the bottom of the display. The method 500 may further comprise switching, by the computing device, the handheld ultrasound imaging device from a sleep mode to an active mode in response to determining that the reading from the first sensor exceeds the threshold.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

The invention claimed is:

1. An ultrasound device, comprising:
a housing configured for handheld use and comprising a plurality of edges;
an ultrasound transducer array coupled to the housing and configured to obtain ultrasound data while positioned adjacent to a body of a patient;
a display coupled to the housing and arranged to display medical information derived from the obtained ultrasound data;
a plurality of sensors coupled to the housing and configured to provide one or more readings representative of a positioning of a hand of an operator around the housing;

an accelerometer disposed within the housing and configured to provide one or more readings representative of an orientation of the housing; and a computing device disposed within the housing, wherein the computing device is in communication with the ultrasound transducer array, the display, the plurality of sensors, and the accelerometer, wherein the computing device is operable to:

enter, based on the one or more readings from the plurality of sensors, an active mode in which the ultrasound transducer array is activatable to obtain the ultrasound data; and use a hierarchical order to control an orientation of the medical information on the display, wherein the hierarchical order comprises:

the one or more readings from the plurality of sensors;

the one or more readings from the accelerometer; and a default orientation setting of the display, such that the computing device uses the one or more readings from the accelerometer to determine the orientation of the medical information only after the one or more readings from the plurality of sensors do not determine the orientation of the medical information, wherein, to use the hierarchical order, the computing device is operable to:

determine, based on the one or more readings from the plurality of sensors, if the positioning of the hand of the operator corresponds to a predefined list of grips, wherein each grip of the predefined list of grips is associated with a respective orientation setting of the display;

in response to determining that the positioning of the hand of the operator corresponds to a first grip in the predefined list of grips, orient the medical information on the display based on the respective orientation setting associated with the first grip;

in response to determining that the positioning of the hand of the operator does not correspond to the predefined list of grips:

compare the one or more readings from the accelerometer to a threshold;

in response to the one or more readings from the accelerometer satisfying the threshold, orient the medical information based on the one or more readings from the accelerometer; and in response to the one or more readings from the accelerometer not satisfying the threshold, orient the medical information based on the default orientation setting.

2. The ultrasound device of claim 1, wherein, to enter the active mode, the computing device is configured to:

switch the ultrasound device from a sleep mode to the active mode.

3. The ultrasound device of claim 2, wherein the ultrasound device expends only enough power to monitor the plurality of sensors while in the sleep mode.

4. The ultrasound device of claim 2, wherein the computing device is further operable to:

power on the display in response to switching the ultrasound device from the sleep mode to the active mode.

5. The ultrasound device of claim 1, wherein, to determine if the positioning of the hand of the operator corresponds to the predefined list of grips, the computing device is operable to:

determine that a thumb of the operator contacts a first edge of the plurality of edges.

6. The ultrasound device of claim 5, wherein, to determine if the positioning of the hand of the operator corresponds to the predefined list of grips, the computing device is further operable to:

determine that a finger of the operator other than the thumb contacts a second edge of the plurality of edges.

7. The ultrasound device of claim 6, wherein the second edge is opposite to the first edge.

8. The ultrasound device of claim 5, wherein, to determine if the positioning of the hand of the operator corresponds to the predefined list of grips, the computing device is further operable to:

determine that an interdigital webbing of the hand of the operator contacts a third edge of the plurality of edges.

9. The ultrasound device of claim 1, wherein the plurality of sensors are capacitance sensors.

10. The ultrasound device of claim 1, wherein the computing device is operable to:

activate the ultrasound transducer array to obtain the ultrasound data.

11. The ultrasound device of claim 1, wherein the computing device is further operable to compare the one or more readings from the plurality of sensors and determine a maximum reading.

12. The ultrasound device of claim 11, wherein a first sensor of the plurality of sensors is disposed on a first edge of the plurality of edges, wherein, to determine that the positioning of the hand of the operator corresponds to the first grip, the computing device is further operable to determine that a reading from the first sensor is the maximum reading, and wherein, with the respective orientation setting associated with the first grip, the medical information is orientated such that the first edge is at a bottom of the display.

13. The ultrasound device of claim 1, wherein the computing device is further operable to change the orientation of the medical information on the display while an orientation of the ultrasound transducer array remains unchanged.

14. The ultrasound device of claim 1, wherein the housing further comprises:

a first surface facing a first direction, the first surface comprising the ultrasound transducer array;

a second surface facing an opposite, second direction, the second surface comprising the display; and a side-facing surface extending between the first surface and the second surface such that the side-facing surface defines a depth of the housing, wherein the side-facing surface comprises the plurality of edges and the plurality of sensors.

15. The ultrasound device of claim 1, wherein the computing device is operable to determine if the positioning of the hand of the operator corresponds to the predefined list of grips based on a stored handedness preference.

16. A method of operating a handheld ultrasound device, comprising:

entering, by a computing device disposed within a housing of the handheld ultrasound device, an active mode in which an ultrasound transducer array coupled to the housing is activatable to obtain ultrasound data, wherein the entering is based on one or more readings from a plurality of sensors coupled to the housing that are representative of a positioning of a hand of an operator around the housing; and using, by the computing device, a hierarchical order to control an orientation of medical information on a display coupled to the housing, wherein the hierarchical order comprises:
  the one or more readings from the plurality of sensors;
  one or more readings from an accelerometer disposed within the housing that are representative of an orientation of the housing; and
  a default orientation setting of the display, such that the computing device uses the one or more readings from the accelerometer to determine the orientation of the medical information only after the one or more readings from the plurality of sensors do not determine the orientation of the medical information,
wherein the using the hierarchical order comprises:
  determining, based on the one or more readings from the plurality of sensors, if the positioning of the hand of the operator corresponds to a predefined list of grips, wherein each grip of the predefined list of grips is associated with a respective orientation setting of the display;
  in response to determining that the positioning of the hand of the operator corresponds to a first grip in the predefined list of grips, orienting the medical information on the display based on the respective orientation setting associated with the first grip;
  in response to determining that the positioning of the hand of the operator does not correspond to the predefined list of grips:
    comparing the one or more readings from the accelerometer to a threshold;
    in response to the one or more readings from the accelerometer satisfying the threshold, orienting the medical information based on the one or more readings from the accelerometer; and
    in response to the one or more readings from the accelerometer not satisfying the threshold, orienting the medical information based on the default orientation setting.

* * * * *